United States Patent [19]

Buckle et al.

[11] 4,005,219
[45] Jan. 25, 1977

[54] PHARMACEUTICAL COMPOSITIONS AND THEIR ADMINISTRATION FOR THE PROPHYLAXIS OF ASTHMA, HAYFEVER AND RHINITIS

[75] Inventors: Derek Richard Buckle, Redhill; Harry Smith, Horsham, both of England

[73] Assignee: Beecham Group Limited, Great Britain

[22] Filed: Mar. 21, 1975

[21] Appl. No.: 560,733

Related U.S. Application Data

[62] Division of Ser. No. 409,164, Oct. 24, 1973, Pat. No. 3,920,725.

[30] Foreign Application Priority Data

Apr. 11, 1974 United Kingdom ............ 52203/74

[52] U.S. Cl. .............................. 424/305; 424/263; 424/331
[51] Int. Cl.² ...................................... A61K 31/215
[58] Field of Search .................. 424/263, 305, 331

[56] References Cited

UNITED STATES PATENTS

| 3,864,493 | 2/1975 | Cairns et al. | 424/283 |
| 3,879,544 | 4/1975 | Reisner et al. | 424/337 |
| 3,883,653 | 5/1975 | Barth | 424/251 |
| 3,885,038 | 5/1975 | Pfister et al. | 424/283 |

OTHER PUBLICATIONS

Cema, et al., Chemical Abstracts, 68:87034q, (1968).
Severina, et al., Chemical Abstracts, 68:29304s.

*Primary Examiner*—Norman A. Drezin

[57] ABSTRACT

Nitro-indane-diones, their production, and pharmaceutical compositions and their administration in forms suitable for the prophylaxis of asthma, hayfever and rhinitis in amounts effective for oral, parenteral and insufflation administration for such forms. The compounds are nitro-indane-diones of the formula:

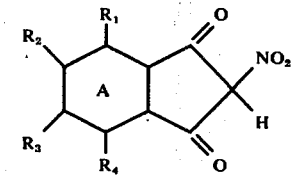

wherein $R_1$, $R_2$, $R_3$ and $R_4$ have certain designated meanings, obtained by nitration of a parent un-nitrated compound and wherein ring A contains 1 or 2 double bonds.

22 Claims, No Drawings

PHARMACEUTICAL COMPOSITIONS AND THEIR ADMINISTRATION FOR THE PROPHYLAXIS OF ASTHMA, HAYFEVER AND RHINITIS

This application is a division of application Ser. No. 409,164 filed Oct. 24, 1973, now U.S. Pat. No. 3,920,725 issued Nov. 18, 1975.

This invention relates to pharmaceutical compositions which are useful in the inhibition of the effects of certain types of antigen-antibody reactions, and are therefore of value in the prophylaxis and treatment of diseases associated allergic or immunological reactions, e.g., certain types of asthma and hay-fever and also in the treatment of rhinitis. The invention also includes novel compounds having such antiallergic activity and a method for their preparation.

According to the present invention, there is provided a compound of formula (I) or a salt thereof:

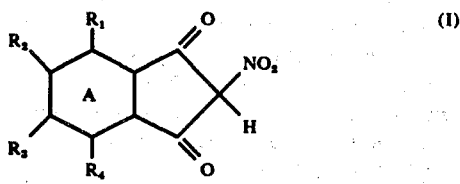

wherein $R_1, R_2, R_3$ and $R_4$ are each hydrogen or alkyl, aryl, alkoxy, aralkyl, acyloxy, heterocyclic, carboxy, alkoxycarbonyl or halogen groups, or any two of the groups $R_1, R_2, R_3$ and $R_4$ may be joined in a carbocyclic or heterocyclic ring system, and wherein the ring marked A is fully saturated or contains 1 or 2 double bonds.

Examples of groups $R_1, R_2, R_3$ and $R_4$ which may be present in the compounds of this invention include methyl, ethyl, n-and iso-propyl, n- sec-, and tert-butyl; methoxy, ethoxy, n-and iso-propoxy, n- sec-, and tert-butoxy, phenyl, benzyl, acetoxy, propionoxy, n-and iso-butyroxy, pyridyl, methoxycarbonyl, ethoxycarbonyl, n-and iso-propoxycarbonyl, fluoro, chloro, bromo, or iodo groups. In addition any two of the groups $R_1, R_2, R_3$ and $R_4$ taken together may represent the residue of a 1,2-phenylene or 1,2-cyclohexylene ring, which may carry one or more of the substituents listed above.

The compounds of this invention may be prepared by a process which comprises nitrating the parent compound of formula (II):

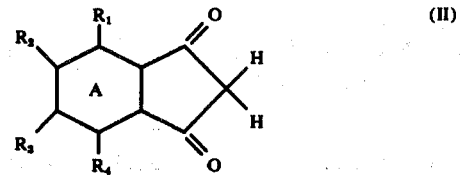

wherein $R_1, R_2, R_3, R_4$ and ring A are as defined with respect to formula (I). The nitration step may be carried out at various temperatures, although usually below 25° C. In general a temperature of from −30° C to +20° C will be suitable, with −20° C being suitable on most occasions. Preferably the nitration step is carried out using fuming nitric acid, but other nitrating agents, such as the nitrous fumes generated with concentrated nitric acid and arsenic oxide, acetic acid and concentrated nitric acid or concentrated nitric acid itself may be used.

The salts of compounds (I) are preferably pharmaceutically acceptable salts e.g., alkali metal salts such as sodium or potassium and salts with organic bases such as amines or amino compounds. Compounds (I) and their salts may exist on occasions as an anhydrous form or as various hydrates.

The invention also includes a pharmaceutical composition comprising a compound of formula (I) above or a pharmaceutically acceptable salt thereof, together with one or more pharmaceutically acceptable carriers.

The compositions of this invention may be presented as a microfine powder for insufflation e.g., as a snuff or in capsules of hard gelatine. They may also be presented together with a sterile liquid carrier for injection. Some of the compounds (I) appear to be active when given orally and thus the compositions of this invention may be in the form of tablets capsules pills or syrups. Preferably the compositions are presented in unit dosage or in a form in which the patient can administer to himself a single dosage unit. If desired a small amount of a bronchodilator compound may be incorporated in the compositions of the invention, both to inhibit the cough response and to provide immediate relief during an asthmatic attack.

The following Examples illustrate the preparation and properties of some of the compounds of this invention.

EXAMPLE 1 a. 5,6-Dimethyl cis-3a,4,7,7a-tetrahydroindane-1,3-dione

A solution of 4-cyclopentene-1,3-dione (5.48g; 0.06 mole) and 2,3-dimethyl butadiene (10.4g; 0.127 mole) in dry benzene (20ml) were treated with a few crystals of 2,5-di-t-butyl hydroquinone and allowed to stand at ambient temperature for 4 days. After refluxing for 15 mins the mixture was cooled and the pale orange solid filtered. Recrystallisation from benzene, methanol afforded the title product as a white solid, m.p. 157°–158° C.

(Found: C, 74.17; H, 7.89; $C_{11}H_{14}O_2$ requires; C 74.13: H 7.92%).

b. 5,6-Dimethyl-2-nitro cis-3a,4,7,7a-tetrahydroindane-1,3-dione

Fuming nitric acid (1.0ml) was added dropwise to a suspension of 5,6-dimethyl cis-3a,4,7,7a-tetrahydroindane-1,3-dione (0.89g; 0.05 mole) in dry ether (8ml.) at −20° C and the mixture maintained at this temperature for 45 mins after the addition. On warming to 5° C a further 0.5ml. of fuming nitric acid was added and the mixture stirred for 1hr. at room temperature. Filtration afforded the 2-nitro derivative as a yellowish solid m.p. (methanol) 156°–157.5° C.

(Found: C, 59.19; H, 5.98; N, 6.05; $C_{11}H_{13}NO_4$ requires; C, 59.19; H, 5.87; N, 6.27%).

EXAMPLE 2 a. 5,6-Dimethyl cis-hexahydroindane-1,3-dione

A solution of 5 6-dimethyl cis-3a,4,7,7a-tetrahydroindane-1,3-dione (1.78g; 0.01 mole) in methanol (15ml.) was added to pre-reduced 10% palladinised charcoal (0.15g) in methanol (15ml.) and the mixture hydrogenated till one equivalent of hydrogen was absorbed. Filtration and evaporation then gave the hexahydroindane dione as a white crystalline solid, m.p. (ethyl acetate, ether) 135°–7° C.

(Found: C, 73.03; H, 8.97; $C_{11}H_{16}O_2$ requires: C, 73.30; H, 8.95%).

b. 5,6-Dimethyl cis-hexahydro-2-nitro indane-1,3-dione

Nitration of 5,6-dimethyl cis-hexahydroindane-1,3-dione as described in example 1b afforded the title product as a white crystalline solid, m.p. (methanol) 169°–170° C.

(Found: C, 58.35; H, 6.77: N, 6.39; $C_{11}H_{15}NO_4$ requires; C, 58.66; H, 6.71; N, 6.22%).

EXAMPLE 3 a. 4,7-Dimethyl cis-3a,4,7,7a-tetrahydroindane-1,3-dione

This was prepared as for example 1(a) using hexa-2,4-diene in place of 2,3-dimethyl butadiene, m.p. (methanol) 210° C.

(Found; C, 74.13; H, 7.99; $C_{11}H_{14}O_2$ requires; C, 74.13; H, 7.92%).

b. 4,7-Dimethyl-2-nitro cis-3a,4,7,7a-tetrahydroindane-1,3-dione

Nitration of 4,7-dimethyl cis-3a,4,7,7a-tetrahydroindane-1,3-dione according to the procedure of example 1 (b) afforded the 2-nitro derivative; m.p. (methanol) 127°–8° C.

(Found; C, 58.85; H, 5.99; N, 6.31; $C_{11}H_{13}NO_4$ requires; C, 59.19; H, 5.87; N, 6.27%).

EXAMPLE 4 a. 4,7-Dimethyl cis hexahydroindane-1,3-dione

A solution of 4,7-dimethyl cis-3a,4,7,7a-tetrahydroindane 1,3-dione in methanol was reduced over 10% palladinised charcoal to give the title compound as a white crystalline solid, m.p. (methanol) 194° C.

(Found; C, 73.28; H, 9.10; $C_{11}H_{16}O_2$ requires; C, 73.30; H, 8.95%).

b. 4,7-Dimethyl cis-hexahydro-2-nitro indane-1,3-dione

Nitration of 4 7-dimethyl cis hexahydroindane-1,3-dione as for the 5,6-dimethyl analogue (example 1(a)) gave the 2-nitro derivative; m.p. (ethanol) 111°–112° C.

(Found; C, 58.45; H, 6.80; N, 6.01; $C_{11}H_{15}NO_4$ requires; C, 58.66; H, 6.71; N, 6.22%).

EXAMPLE 5 a. 4-Carboxy cis-3a,4,7,7a-tetrahydroindane-1,3-dione

A solution of 4-cyclopentene-1,3-dione (9 6g; 0.1 mole) in dry benzene (30ml.) was added to 1-carboxy butadiene (9 8g; 0.1 mole) and a few crystals of 2,5-di-t-butyl hydroquinone added. The orange solution was stood at room temperature for 3 days and evaporated to small bulk to induce crystallisation. Filtration followed by trituration with anhydrous ether gave the desired product, m.p. 182° C. (H. O. House and G. H. Rasmunsen J. Org. Chem., 1963, 28, 27 quote m.p. 191° C).

b. 4-Carboxy-2-nitro cis-3a,4,7,7a-tetrahydroindane-1,3-dione

To a stirred suspension of 4-carboxy cis-3a,4,7,7a-tetrahydroindane-1,3-dione (0.585g; 0.003 mole) in dry ether (5 ml.) at 5° C was added fuming nitric acid (1.0ml.) dropwise. After stirring 1hr. at 5° C the mixture was kept for 2hrs. at room temperature, filtered and washed well with dry ether to afford analytically pure title compound, m.p. 175° C (decomp.).

(Found; C,50.09; H, 3.88, N, 5.71; $C_{10}H_9NO_6$ requires; C, 50.22; H, 3.79; N, 5.86%).

EXAMPLE 6 a. Tricyclo [5,2,1,0$^{2,6}$] dec-8-ene-3,5-dione

A solution of 4-cyclopentene-1,3-dione (5 84g; 0.06 mole) in anhydrous benzene (20ml) was treated with freshly distilled cyclopentadiene (7.3g; 0.122 mole) together with a few crystals of 2,5-di-t-butyl hydroquinone. An immediate reaction ensued with concommitant crystallisation of the product. After standing at room temperature for 3 days the title compound was filtered and recrystallised from methanol, m.p. 183° C.

(Found; C, 73.84; H, 6.26; $C_{10}H_{10}O_2$ requires; C, 74.06; H, 6.22%).

b. 4-Nitro tricyclo [5,2,1,0$^{2,6}$] dec-8-ene-3,5-dione

Nitration of tricyclo [5,2,1,0$^{2,6}$] dec-8-ene-3,5-dione according to example 1b afforded the 4-nitro derivative, m.p. (methanol) 195° C (decomp.).

(Found; C, 58.17; H, 4.49; N, 6.48; $C_{10}H_9NO_4$ requires; C, 57.97; H, 4.38; N, 6.76%).

EXAMPLE 7 a. Tricyclo [5,2,1,0$^{2,6}$] decane-3,5-dione

Reduction of tricyclo [5,2,1,0$^{2,6}$] dec-8-ene-3,5-dione over 10% palladinised charcoal as described in example 2a gave the dihydro product, m.p. (methanol) 175°–177° C.

(Found; C, 73.15; H, 7.51; $C_{10}H_{12}O_2$ requires; C, 73.15; H, 7.37%).

b. 4-Nitro tricyclo [5,2,1,0$^{2,6}$] decane-3,5-dione

To a stirred suspension of tricyclo [5,2,1,0$^{2,6}$] decane-3,5-dione (0.82g; 0.05 mole) in dry ether (8ml.) was added fuming nitric acid (1ml.) at −20° C. After stirring for 1hr. at 20° C the solid was filtered, washed with cold, dry ether and recrystallised from methanol, m.p. 167° C.

(Found; C, 57.69; H, 5.49; N, 6.46; $C_{10}H_{11}NO_4$ requires; C, 57.41; H, 5.30; N, 6.70%).

EXAMPLE 8 a. 4-Methyl-cis-3a,4,7,7a-tetrahydroindane-1,3-dione

A solution of 4-cyclopentene-1,3-dione (5.84g; 0.06 mole) in dry benzene (20ml.) was stood for 4 days with 1,3-pentadiene (8.9g; 0.122 mole) and a little 2,5-di-t-butyl hydroquinone (10mg.) and the crystalline solid filtered off and recrystallised from methanol to yield the title dione, m.p. 139°–40° C.

(Found; C, 72.96; H, 7.51; $C_{10}H_{12}O_2$ requires; C, 73.15; H, 7.34%).

b. 4-Methyl-2-nitro-cis-3a,4,7,7a-tetrahydroindane-1,3-dione

Nitration of 4-methyl-cis-3a,4,7,7a-tetrahydroindane-1,3-dione as described in example 7b afforded the 2-nitro derivative, m.p. (methanol) 101° C.

(Found; C, 57.13; H, 5.30; N, 6.47; $C_{10}H_{11}NO_4$ requires; C, 57.41; H, 5.30; N, 6.70%).

EXAMPLE 9 a. 4-Carbomethoxy-cis-3a,4,6,7a-tetrahydroindane-1,3-dione

The reaction of methyl penta-2,4-dienoate with cyclopentene-1,3-dione according to example 1a, gave the title Diels-Alder adduct, m.p. (methanol) 195°–196° C.

(Found; C 63.52; H, 5.77; $C_{11}H_{12}O_4$ requires; C, 63.45; H, 5.81%).

b. 4-Carbomethoxy-2-nitro-cis-3a,4,7,7a-tetrahydroindane-1,3-dione

Treatment of 4-carbomethoxy-cis-3a,4,7,7a-tetrahydroindane-1,3-dione with fuming nitric acid at −20° C yielded the 2-nitro derivative, m.p. (methanol) 139° C.

(Found; C, 52.14; H, 4.32; N, 5.46; $C_{11}H_{11}NO_6$ requires; C, 52.18; H, 4.38; N, 5.53%).

EXAMPLE 10 a. 4-Acetoxy-cis-hexahydroindane-1,3-dione

Catalytic reduction of 4-acetoxy-cis-3a,4,7,7a-tetrahydroindane-1,3-dione (m.p. 168° C) according to example 2a afforded the hexahydro derivative, m.p. (methanol) 135°–138° C.

(Found; C, 62.92; H, 6.89; $C_{11}H_{14}O_4$ requires; C, 62.85; H, 6.71%).

b. 4-Acetoxy-cis-hexahydro-2-nitro-indane-1,3-dione

Nitration of 4-acetoxy-cis-hexahydroindane-1,3-dione at 20° C gave the title compound, m.p. (methanol) 147° C.

(Found; C, 51.59; H, 5.22; N, 5.49; $C_{11}H_{13}NO_6$ requires; C, 51.76; H, 5.13; N, 5.49%).

EXAMPLE 11 a. 4-Methyl-cis-hexahydroindane-1,3-dione

Reduction of 4-methyl cis-3a,4,7,7a-tetrahydroindane-1,3-dione over 10% palladinised charcoal as described in example 2a afforded the dihydro product, m.p. (MeOH) 122° C.

(Found; C, 72.48; H, 8.48; $C_{10}H_{14}O_2$ requires; C, 72.26; H, 8.49%).

b. 4-Methyl-2-nitro-cis-hexahydroindane-1,3-dione

Nitration of a stirred suspension of 4-methyl cis-hexahydroindane-1,3-dione as described in example 1b gave the 2-nitro derivative m.p. (MeOH) 118°–120° C.

(Found; C 56.41; H,6.12; N,6 69; $C_{10}H_{13}NO_4$ requires; C, 56. 86; H, 6,20; N, 6.63%).

EXAMPLE 12 a. Tricyclo $[5,2,2,0^{2,6}]$ undec-8-ene-3,5dione

A solution of 4-cyclopentene-1,3-dione (7.0g; 0.073 mole) in dry benzene (20ml.) was added to 1,3-cyclohexadiene (12g; 0.15 mole). After addition of a few crystals of 2,5-ditert-butyl hydroquinone the stoppered mixture was stood at room temperature for 4 days. Removal of the solid and recrystallisation from methanol gave the adduct m.p. 264°.

(Found; C,74.82; H,7.08; $C_{11}H_{12}C_2$ requires; C,74.98; H,6.86%).

b. 4-Nitro tricyclo $[5,2,2,0^{2,6}]$ undec-8-ene-3,5-dione

Tricyclo $[5,2,2,0^{2,6}]$ undec-8-ene-3,5-dione nitrated at −20° C as described gave the 4-nitro derivative m.p. (MeOH) 206° C.

(Found; C,59.63; H,5.11; N6,03; $C_{11}H_{11}NO_4$ requires C,59.73; H,5.01; N,6.33%).

EXAMPLE 13 a. Tricyclo $[5,2,2,0^{2,6}]$ undecane-3,5-dione

Reduction of tricyclo $[5,2,2,0^{2,6}]$ undec-8-ene-3,5-dione over 10% palladinised charcoal as described in example 2a gave the title compound; m.p. (MeOH) 254°–5° C.

(Found; C, 73.94 H,7.90; $C_{11}H_{14}O_2$ requires; C,74.13; H,7.92%).

b. 4-Nitro tricyclo $[5,2,2,0^{2,6}]$ undecane-3,5-dione

Tricyclo $[5,2,20^{2,6}]$ undecane-3,5-dione was nitrated at −20° C as described in example 1b. The product had m.p. (MeOH) 199° C.

(Found; C,59,21; H,5.84; N6.18; $C_{11}H_{13}NO_4$ requires; C,59.19; H,5.87; N, 6.27%).

EXAMPLE 14

Biological Results

All of the 2-nitro indane-1,3-diones prepared in the preceeding Examples were submitted for biological testing. The test system was the Rat Passive Cutaneous Anaphylaxis (PCA) test described below in (II).

I. Serum containing heat labile homocytotropic antibody was raised in rats by a method similar to that used by Mota. (I. Mota Immunology 1964, 7, 681).

Male Wistar rats of 250-300g, were injected intraperitoneally with 0.5ml. of *Bordetella pertussis* vaccine (containing 4 × $10^{10}$ dead oranism per ml. and subcutaneously with 0.5ml. of an emulsion of 100mg. of ovalbumin in 2ml of saline and 3ml of incomplete Freunds' adjuvant. Rats were bled by cardiac puncture on day 18, the blood was pooled and separated and serum stored at −20° and thawed only once before use.

II. The P.C.A. test was similar to that described by Ovary and Bier (A. Ovary and O. E. Bier. Proc. Soc. Exp. Biol. Med. 1952, 81, 584) and Goose and Blair (J. Goose and A. M. J. N Blair Immunology 1969, 16, 749).

0.1ml of each of six twofold serial dilutions of the serum in 0.9% saline were injected intradermally into separate sites on the shaved dorsal surface of 250–350g. Wistar rats. 72 hours later the animals were challenged by i.v. injection of 0.3ml of 1% ovalbumin mixed with 0.1ml of a 5% solution of pontamine sky blue dye both in isotonic saline buffered with pH. 7.2 Sorenson buffer (P.B.S.). The rats were killed after 20 minutes and the diameter of the blue wheals at the antibody injection sites were measured. The starting dilution of the serum was adjusted so that there was no response, after challenge, at the site of injection of the highest dilution and a maximum response at the lowest dilution. Typically six twofold serial dilutions of the serum from one-fourth to one-twenty-eighth were used.

Compounds were tested for their ability to reduce the diameter of the wheals at the injection sites of dilutions of antibody which on all the controls have less than maximum response. Amounts of the compounds were administered to rats each amount to a test group of six animals at a specified time prior to intravenous challenge with ovalbumin. The diameters of the blue wheals which developed on the test group of animals were compared with those on a control group of six animals treated in the same way as the test group, but which had not received the compound under test.

% Inhibition of P.C.A. = 100 (1 − a/b)

a = The mean of the sum of the diameters of the wheals produced in the test group of animals at those antibody sites where all the control group of animals gave less than maximum response.

b = The mean of the sum of diameters of the wheals produced in the control group of animals at those antibody sites where all the animals in the group gave less than maximum response.

The preferred method of administration was as a solution of the test compound dissolved in pH 7.2 buffer and neutralised with sodium bicarbonate. For those compounds having insoluble sodium salts, the salts were isolated by reaction of the free nitro compound with 2.5N sodium hydroxide and the filtered sodium salt washed free of alkali with water. The dried salts were then administered as a suspension in 1% methyl cellulose.

| Test compound Product of example No. | Dose mg/kg | Time (Mins) | %Inhibition of PCA response |
|---|---|---|---|
| 1(b) | 25 | 0 | 16 |
| | 100 | 0 | 61 |
| | 25 | 30 | 6 |
| | 100 | 30 | 42 |
| 2(b) | 25 | 0 | 7 |
| | 100 | 0 | 31 |
| | 25 | 30 | 6 |
| | 100 | 30 | 37 |
| 3(b) | 25 | 0 | −8 |
| | 100 | 0 | −8 |
| | 25 | 30 | 7 |
| | 100 | 30 | −1 |
| 4(b) | 25 | 0 | 4 |
| | 100 | 0 | 19 |
| | 25 | 60 | 13 |
| | 100 | 60 | 11 |
| 5(b) | 25 | 0 | 2 |
| | 100 | 0 | −3 |
| | 25 | 30 | −1 |
| | 100 | 30 | −6 |
| 6(b) | 25 | 0 | −9 |
| | 100 | 0 | 4 |
| | 25 | 60 | −9 |
| | 100 | 60 | 17 |
| 7(b) | 25 | 0 | 8 |
| | 100 | 0 | 26 |
| | 25 | 30 | −3 |
| | 100 | 30 | 9 |
| 8(b) | 25 | 0 | 12 |
| | 100 | 0 | 41 |
| | 25 | 30 | 13 |
| | 100 | 30 | 52 |
| 9(b) | 25 | 0 | 2 |
| | 100 | 0 | 10 |
| | 25 | 30 | −9 |
| | 100 | 30 | −5 |
| 10(b) | 25 | 0 | 12 |
| | 100 | 0 | 11 |
| | 25 | 30 | 17 |
| | 100 | 30 | 20 |
| 11(b) | 25 | 0 | −13 |
| | 100 | 0 | 11 |
| | 25 | 30 | −8 |
| | 100 | 30 | 17 |

-continued

| Test compound Product of example No. | Dose mg/kg | Time (Mins) | %Inhibition of PCA response |
|---|---|---|---|
| 12(b) | 25 | 0 | 0 |
| | 100 | 0 | −3 |
| | 25 | 30 | 29 |
| | 100 | 30 | 32 |
| 13(b) | 25 | 0 | 14 |
| | 100 | 0 | 8 |
| | 25 | 30 | 13 |
| | 100 | 30 | 29 |

What we claim is:

1. A pharmaceutical composition in a form suitable for oral, parenteral or insufflation administration to humans which comprises an amount of a compound of the formula (I) or a salt thereof:

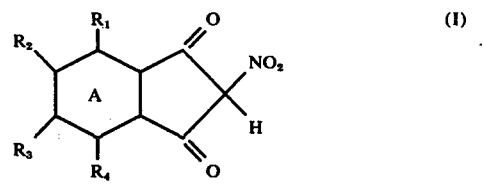

wherein $R_1$, $R_2$, $R_3$ and $R_4$ are each hydrogen, lower alkyl, phenyl, benzyl, lower alkoxy, lower acyloxy, carboxy, lower alkoxycarbonyl or halogen, and wherein the ring marked A contains 1 or 2 double bonds, sufficient to be effective for the prophylaxis of asthma, hayfever or rhinitis in combination with a pharmaceutically-acceptable, nontoxic, inert diluent or carrier suitable for said administration form.

2. A composition according to claim 1 wherein $R_1$, $R_2$, $R_3$ and $R_4$ are each hydrogen, methyl, ethyl, n- and iso-propyl, n-, sec- and tert-butyl, methoxy, ethoxy, n- and iso-propoxy, n-, sec- and tert-butoxy, phenyl, benzyl, acetoxy, propionoxy, n- and iso-butyroxy, methoxycarbonyl, ethoxycarbonyl, n- and iso-propoxycarbonyl, fluoro, chloro, bromo or iodo groups.

3. A composition according to claim 1 wherein the compound is 5,6-dimethyl-2-nitro cis-3a,4,7,7a-tetrahydroindane-1,3-dione.

4. A composition according to claim 1 wherein the compound is 5,6-dimethyl cis-hexahydro-2-nitro indane-1,3-dione.

5. A composition according to claim 1 wherein the compound is 4,7-dimethyl 2-nitro cis-3a,4,7,7a-tetrahydroindane-1,3-dione.

6. A composition according to claim 1 wherein the compound is 4,7-dimethyl cis-hexahydro-2-nitro indane-1,3-dione.

7. A composition according to claim 1 wherein the compound is 4-carboxy-2-nitro cis-3a,4,7,7a-tetrahydroindane-1,3-dione.

8. A composition according to claim 1 wherein the compound is 4-methyl-2-nitro-cis-3a,4,7,7a-tetrahydroindane-1,3-dione.

9. A composition according to claim 1 wherein the compound is 4-carbomethoxy-2-nitro-cis-3a,4,7,7a-tetrahydroindane-1,3-dione.

10. A composition according to claim 1 wherein the compound is 4-acetoxy-cis-hexahydro-2-nitro-indane-1,3-dione.

11. A composition according to claim 1 wherein the compound is 4-methyl-2-nitro-cis-hexahydroindane-1,3-dione.

12. A method for the prophylaxis of asthma, hayfever and rhinitis in humans which comprises administering to a human in need thereof orally, parenterally or by insufflation an amount of the composition of claim 1 sufficient to be effective for the prophylaxis of asthma, hayfever and rhinitis.

13. A method for the prophylaxis of asthma, hayfever and rhinitis in humans which comprises administering to a human in need thereof orally, parenterally or by insufflation an amount of the composition of claim 2 sufficient to be effective for the prophylaxis of asthma, hayfever and rhinitis.

14. A method for the prophylaxis of asthma, hayfever and rhinitis in humans which comprises administering to a human in need thereof orally, parenterally or by insufflation an amount of the composition of claim 10 sufficient to be effective for the prophylaxis of asthma, hayfever and rhinitis.

15. A method for the prophylaxis of asthma, hayfever and rhinitis in humans which comprises administering to a human in need thereof orally, parenterally or by insufflation an amount of the composition of claim 11 sufficient to be effective for the prophylaxis of asthma, hayfever and rhinitis.

16. A method for the prophylaxis of asthma, hayfever and rhinitis in humans which comprises administering to a human in need thereof orally, parenterally or by insufflation an amount of the composition of claim 12 sufficient to be effective for the prophylaxis of asthma, hayfever and rhinitis.

17. A method for the prophylaxis of asthma, hayfever and rhinitis in humans which comprises administering to a human in need thereof orally, parenterally or by insufflation an amount of the composition of claim 13 sufficient to be effective for the prophylaxis of asthma, hayfever and rhinitis.

18. A method for the prophylaxis of asthma, hayfever and rhinitis in humans which comprises administering to a human in need thereof orally, parenterally or by insufflation an amount of the composition of claim 14 sufficient to be effective for the prophylaxis of asthma, hayfever and rhinitis.

19. A method for the prophylaxis of asthma, hayfever and rhinitis in humans which comprises administering to a human in need thereof orally, parenterally or by insufflation an amount of the composition of claim 17 sufficient to be effective for the prophylaxis of asthma, hayfever and rhinitis.

20. A method for the prophylaxis of asthma, hayfever and rhinitis in humans which comprises administering to a human in need thereof orally, parenterally or by insufflation an amount of the composition of claim 18 sufficient to be effective for the prophylaxis of asthma, hayfever and rhinitis.

21. A method for the prophylaxis of asthma, hayfever and rhinitis in humans which comprises administering to a human in need thereof orally, parenterally or by insufflation an amount of the composition of claim 19 sufficient to be effective for the prophylaxis of asthma, hayfever and rhinitis.

22. A method for the prophylaxis of asthma, hayfever and rhinitis in humans which comprises administering to a human in need thereof orally, parenterally or by insufflation an amount of the composition of claim 20 sufficient to be effective for the prophylaxis of asthma, hayfever and rhinitis.

* * * * *

UNITED STATES PATENT AND TRADEMARK OFFICE
CERTIFICATE OF CORRECTION

PATENT NO. : 4,005,219
DATED : January 25, 1977
INVENTOR(S) : Derek Richard Buckle et al Page 1 of 2

It is certified that error appears in the above-identified patent and that said Letters Patent are hereby corrected as shown below:

The line under foreign application priority data should read --November 11, 1972 United Kingdom 52203/72--

| | |
|---|---|
| Claim 14, line 4 | "claim 10" should read --claim 3--; |
| Claim 15, line 4 | "claim 11" should read --claim 4--; |
| Claim 16, line 4 | "claim 12" should read --claim 5--; |
| Claim 17, line 4 | "claim 13" should read --claim 6--; |
| Claim 18, line 4 | "claim 14" should read --claim 7--; |
| Claim 19, line 4 | "claim 15" should read --claim 8--; |
| Claim 20, line 4 | "claim 18" should read --claim 9--; |
| Claim 21, line 4 | "claim 17" should read --claim 10--; |

UNITED STATES PATENT OFFICE
CERTIFICATE OF CORRECTION

Patent No. 4,005,219     Dated January 25, 1977

Inventor(s) Derek Richard Buckle et al.     Page 2 of 2

It is certified that error appears in the above-identified patent and that said Letters Patent are hereby corrected as shown below:

Claim 22, line 4     "claim 20" should read -- claim 11 --

Signed and Sealed this sixteenth Day of August 1977

[SEAL]

Attest:

RUTH C. MASON
*Attesting Officer*

C. MARSHALL DANN
*Commissioner of Patents and Trademarks*